(12) United States Patent (10) Patent No.: US 9,014,329 B2
Sagoh et al. (45) Date of Patent: Apr. 21, 2015

(54) X-RAY COMPUTED TOMOGRAPHY APPARATUS

(75) Inventors: Tomoe Sagoh, Tochigi-ken (JP);
Takayuki Yamazaki, Tochigi-ken (JP);
Michito Nakayama, Tochigi-ken (JP);
Atsushi Hashimoto, Tochigi-ken (JP);
Takeshi Miyagi, Kanagawa-ken (JP)

(73) Assignees: Kabushiki Kaisha Toshiba, Tokyo (JP);
Toshiba Medical Systems Corporation, Otawara-shi (JP)

(*) Notice: Subject to any disclaimer, the term of this patent is extended or adjusted under 35 U.S.C. 154(b) by 105 days.

(21) Appl. No.: 13/165,380

(22) Filed: Jun. 21, 2011

(65) Prior Publication Data

US 2011/0311023 A1 Dec. 22, 2011

(30) Foreign Application Priority Data

Jun. 21, 2010 (JP) .................. P2010-140806

(51) Int. Cl.
*A61B 6/03* (2006.01)
*A61B 6/00* (2006.01)
*H04N 5/32* (2006.01)
*H04N 5/357* (2011.01)

(52) U.S. Cl.
CPC .............. *A61B 6/4208* (2013.01); *A61B 6/032* (2013.01); *A61B 6/4488* (2013.01); *A61B 6/54* (2013.01); *A61B 6/585* (2013.01); *H04N 5/32* (2013.01); *H04N 5/357* (2013.01)

(58) Field of Classification Search
CPC ...................................... G01T 1/2018
USPC ................................... 378/19, 98.8
See application file for complete search history.

(56) References Cited

U.S. PATENT DOCUMENTS

| | | | |
|---|---|---|---|
| 5,521,387 A * | 5/1996 | Riedner et al. | 250/367 |
| 5,970,113 A * | 10/1999 | Crawford et al. | 378/19 |
| 6,954,514 B2 * | 10/2005 | Wischmann et al. | 378/19 |
| 7,078,702 B2 * | 7/2006 | Ringermacher et al. | 250/370.11 |
| 2004/0071259 A1 * | 4/2004 | Lacey et al. | 378/19 |
| 2005/0100128 A1 * | 5/2005 | Hilderscheid et al. | 378/19 |
| 2008/0069296 A1 * | 3/2008 | Joshi et al. | 378/19 |
| 2008/0116388 A1 * | 5/2008 | Joshi et al. | 250/370.15 |
| 2008/0295879 A1 * | 12/2008 | Atanackovic | 136/238 |
| 2009/0167406 A1 * | 7/2009 | Endo | 327/336 |
| 2009/0199887 A1 * | 8/2009 | Johnson et al. | 136/239 |

* cited by examiner

*Primary Examiner* — David J Makiya
*Assistant Examiner* — Danielle Fox
(74) *Attorney, Agent, or Firm* — Oblon, McClelland, Maier & Neustadt, L.L.P.

(57) ABSTRACT

An X-ray CT apparatus includes an X-ray source configured to generate an X-ray; a scintillator configured to convert the X-ray into a fluorescent; a substrate including a plurality of photosensitive elements configured to convert the fluorescent into an electric charge; a temperature sensor formed on the surface of the substrate; a heat element formed on the surface of the substrate; and a controller configured to control a temperature of the photodiode by adjusting an electric current of the heat element.

13 Claims, 11 Drawing Sheets

X-RAY COMPUTED TOMOGRAPHY APPARATUS

CROSS-REFERENCE TO RELATED APPLICATION

This application is based upon and claims the benefit of priority from Japanese Patent Application No. 2010-140806, filed on Jun. 21, 2010, the entire contents of which are incorporated herein by reference.

FIELD

The present embodiments relate to an X-ray CT apparatus including an X-ray detector and a data acquisition system (DAS), in which the temperature of a photodiode array (PDA) of the X-ray detector is controlled.

BACKGROUND

An X-ray CT apparatus includes an X-ray source and an X-ray detector, which are disposed interposing an object in an opposing manner. The X-ray detector includes multiple channels (M channels) of detection elements along a direction orthogonal to the longitudinal direction of a table-top, which is the direction of the body axis of the object.

While various types of X-ray detectors are available, a scintillation detector, which has potential for downsizing, is generally used for X-ray CT apparatuses. Each detection element of the scintillation detector includes a scintillator and a photosensor, such as a PDA. The scintillator absorbs X-rays that are collimated in a preceding stage, and generates fluorescence through the absorption. The PDA converts the fluorescence into an electric signal and outputs the electric signal to a data acquisition system (DAS) That is, according to an X-ray CT apparatus, an X-ray beam is delivered in a fan shape to a section (hereafter, referred to as a "slice plane") of the object from the X-ray source so that X-ray beams that have been transmitted through a certain slice plane of the object are converted into an electric signal for every detection element of the X-ray detector, thereby allowing the acquisition of transmission data.

Further, compared to the above described single-slice X-ray CT apparatus, a multi-slice X-ray CT apparatus includes, besides M channels of detection elements, multiple rows (N rows) of detection elements along the body axis of the object, in the X-ray detector. The X-ray detector of the multi-slice X-ray CT apparatus is configured as a two-dimensional detector for X-ray CT having M channels x N rows of detection elements in total.

FIG. 11 is a side view showing an outline of the configuration of the periphery of an X-ray detector and a DAS in a background X-ray CT apparatus.

FIG. 11 shows an X-ray detector (a scintillation detector) 61, a DAS 62, a thermal shield 63 and a heater 64 which are disposed between the X-ray detector 61 and the DAS 62, and cooling fans 65a and 65b which are disposed in the periphery of the X-ray detector 61 and the DAS 62, in a background X-ray CT apparatus. As shown in FIG. 11, the X-ray detector 61 includes a collimator (N collimators corresponding to N rows) 71 which collimates the X rays that have been transmitted through an object, a detection element (N detection elements corresponding to N rows) 72 which generates an electric signal based on the X rays in a subsequent stage of the collimator 71. The detection element 72 includes a scintillator (N scintillators) 81 and a PDA (N PDAs) 82. The DAS 62, which is disposed in a subsequent stage of the PDA 82, converts and amplifies the electric signal of the PDA 82 into a voltage signal.

The collimator 71 and the detection element 72, which make up the X-ray detector 61, are configured as one body and are thermally shielded from the DAS 62, in which temperature significantly fluctuates, via a thermal shield 63 to keep the PDA 82 of the detection element 72 at a constant temperature. Alternatively, the collimator 71 and the detection element 72 are configured as one body and are accommodated in a case as the thermal shield 63 to keep the PDA 82 of the detection element 72 at a constant temperature. Then, temperature control of the PDA 82 is performed by heating the PDA 82, which has no effect on the temperature fluctuation of the DAS 62, with the heater 64 of about 100 to about 150 [W] and also cooling the PDA 82 with the cooling fan 65a. The temperature of the PDA 82 is controlled, for example, in a range of 40±1° C. which is higher than the room temperature, with the heater 64 and the cooling fan 65a. It is possible to maintain the image quality of CT images by controlling the temperature of the PDA 82.

On the other hand, in some cases, the substrate temperature of the DAS 62 rises to about 60 to about 90° C. due to generated heat, leading to a malfunction of the DAS 62. To prevent an excessive temperature rise of the DAS 62, a cooling fan 65b for cooling the DAS 62 is attached to the substrate of the DAS 62. Thus, the device is configured such that there is no excessive temperature rise in the DAS 62.

As so far described, to control the temperature of the X-ray detector 61, while the thermal shield 63 is used to shield exhaust heat of the DAS 62, heating equipment is provided on the side of the PDA 82 and, at the same time, cooling equipment is provided on the side of the DAS 62.

Thus, the background X-ray CT apparatus causes a waste of electric power in that, on one hand, heating of the PDA 82 is performed while shielding exhaust heat of the DAS 62 and, on the other hand, cooling of the PDA 82 is performed to control the temperature of the detection element of the X-ray detector 61.

Moreover, as the DAS 62 becomes more highly integrated and thereby downsized in recent years, it is required from a viewpoint of performance enhancement that the X-ray detector 61 and the DAS 62 are installed adjacent to each other. As an extreme of this configuration, it is conceivable that the X-ray detector 61 and the DAS 62 are configured to be a unitary structure. However, if a thermal shield is not installed in the background X-ray CT apparatus, the exhaust heat of the DAS 62 will directly affect the temperature of the PDA 82 making it difficult to keep the PDA 82 at a constant temperature. Thus, since installing a thermal shield is a necessity in the background X-ray CT apparatus, it is difficult to achieve a unitary structure of the X-ray detector 61 and the DAS 62. Further, if no heater is installed in the background X-ray CT apparatus, it cannot be expected that the temperature of the PDA 82 is always high enough. Thus, since installing a heater 64 is a necessity in the background X-ray CT apparatus, it is difficult to achieve a unitary structure of the X-ray detector 61 and the DAS 62.

In addition, disposing a heater 64 in the vicinity of the X-ray detector 61 may result in an ill effect that the heater 64 acts as a noise source.

DETAILED DESCRIPTION

An X-ray CT apparatus of the present embodiment will be described with reference to the appended drawings.

To solve the above-described problems recognized by the present inventors, the X-ray CT apparatus according to the present embodiment includes an X-ray source configured to generate an X-ray; a scintillator configured to convert the X-rays into a fluorescent; a substrate including a plurality of photosensitive elements configured to convert the fluorescent into an electric charge; a temperature sensor formed on the surface of the substrate; a heat element formed on the surface of the substrate; and a controller configured to control a temperature of the photodiode by adjusting an electric current of the heat element.

There are various types of X-ray CT apparatuses of the present embodiment, such as a ROTATE/ROTATE type in which an X-ray tube and an X-ray detector rotate as one body around an object, a STATIONARY/ROTATE type in which a large number of detection elements are arrayed in a ring-shape, and only the X-ray tube rotates around the object, and the like. The present invention can be applied to any of those types. Hereafter, the ROTATE/ROTATE type which is currently in a mainstream position will be described.

Further, the current mainstream structure of the mechanism for converting an incoming X-ray into electric charge includes an indirect conversion type in which an X-ray is converted into light with a fluorescent body such as a scintillator, etc., and the light is converted into electric charges with a photoelectric conversion element such as a photodiode, etc., and a direct conversion type in which the generation of an electron-hole pair in a semiconductor and the transfer thereof to an electrode, that is, a photoconductive phenomenon, is utilized.

In addition, in recent years, progress has been made in the commercialization of a so-called multi-tube type X-ray CT apparatus, in which a plurality of pairs of the X-ray tube and the X-ray detector are mounted on a rotary ring, and the development of peripheral technologies thereof has been in progress. The X-ray CT apparatus of the present embodiment can be applied to either of a single-tube type X-ray CT apparatus, or a multi-tube type X-ray CT apparatus. Here, description will be made supposing a single-tube type X-ray CT apparatus.

Figure 1:
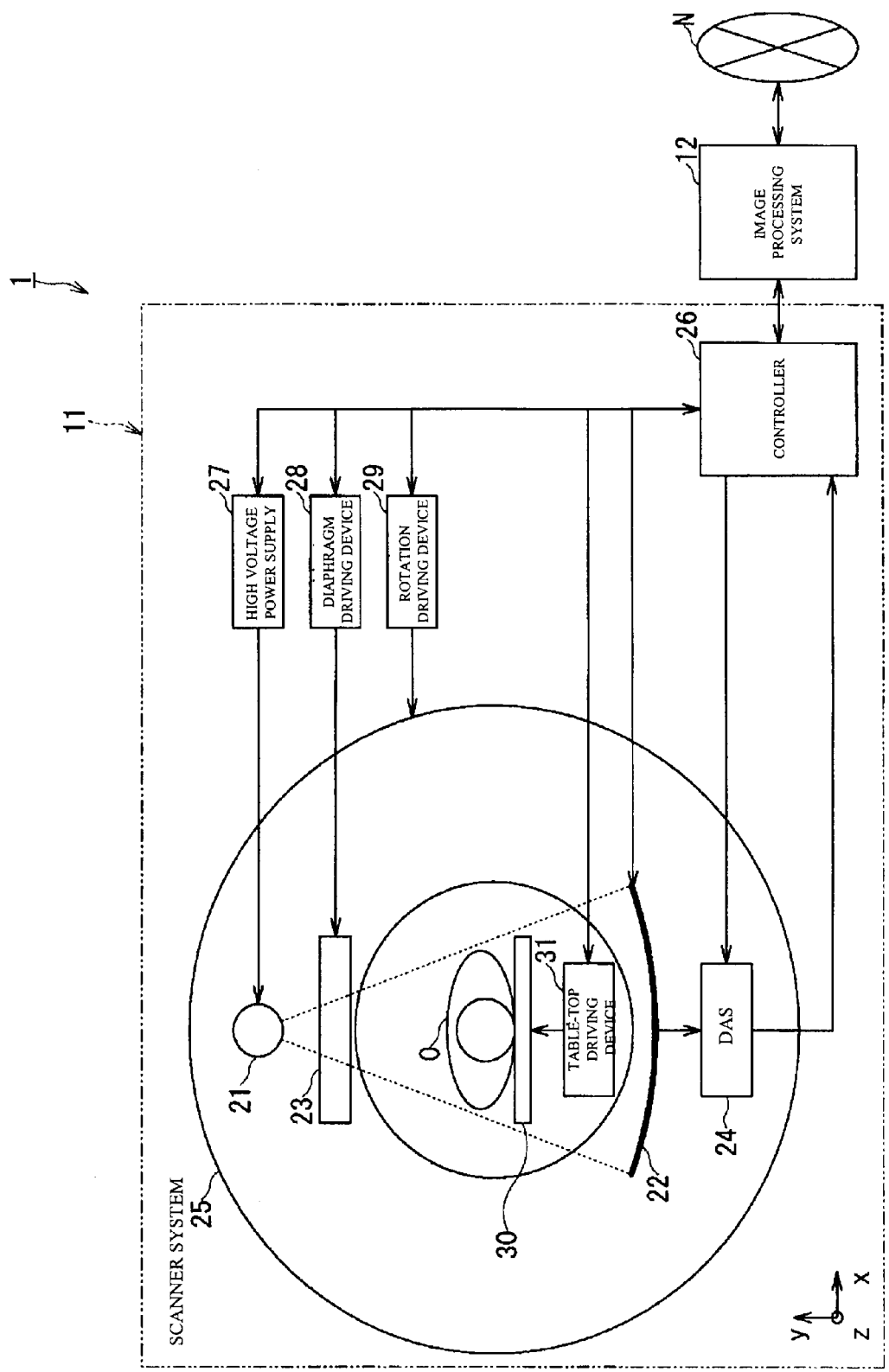
FIG. 1 is a hardware configuration diagram showing an X-ray CT apparatus of a present embodiment.

FIG. 1 is a hardware configuration diagram showing an X-ray CT apparatus of a present embodiment.

FIG. 1 shows an X-ray CT apparatus 1 of the embodiment. The X-ray CT apparatus 1 broadly includes a scanner system 11 and an image processing system 12. The scanner system 11 of the X-ray CT apparatus 1 is generally installed in an examination room, and is configured to generate transmission data of the X-ray relating to an exposure region of an object (human body) O. On the other hand, the image processing system 12 is generally installed in a control room adjacent to an examination room, and is configured to generate projection data based on the transmission data and to generate and display a reconstructed image.

The scanner system 11 of the X-ray CT apparatus 1 includes an X-ray tube 21 as an X-ray source, an X-ray detector (a scintillation detector) 22, a diaphragm (collimator) 23, a DAS (data acquisition system) 24, a rotating portion 25, a controller 26, a high voltage power supply 27, a diaphragm driving device 28, a rotation driving device 29, a table-top 30, and a table-top driving device (a bed system) 31.

The X-ray tube 21 delivers X-rays toward the X-ray detector 22 according to the tube voltage supplied from the high voltage power supply 27. The X-rays delivered from the X-ray tube 21 form cooling fan-beam X-rays and cone-beam X-rays.

The X-ray detector 22 is an X-ray detector of one-dimensional array type which includes multiple (M) channels in a direction (channel direction) orthogonal to a longitudinal direction of the table-top, which is the body axis direction, and one row of detection elements in a slice direction (row direction). Alternatively, the X-ray detector 22 is an X-ray detector of two-dimensional array type (also referred to as a multi-slice type detector) which includes detection elements of matrix form, that is, M channels and multiple (N) rows in the slice direction. The X-ray detector 22 detects X-rays that are delivered from the X-ray tube 21 and that have transmitted through the object O.

The diaphragm 23 is adapted to adjust a range to be irradiated in the slice direction with X-rays delivered from the X-ray tube 21. That is, it is possible to vary the range to be irradiated with X-rays in the slice direction by adjusting the opening of the diaphragm 23 with the diaphragm driving device 28.

The DAS 24 converts and amplifies an electric signal of the transmission data detected by each detection element of the X-ray detector 22 into a voltage signal, and further converts it into a digital signal. The output data of the DAS 24 is provided to the image processing system 12 via the controller 26.

The rotating portion 25 is accommodated in a gantry (not shown) of the scanner system 11, and holds the X-ray tube 21, the X-ray detector 22, the diaphragm 23, and the DAS 24 in one body. The rotating portion 25 is configured so as to be able to rotate the X-ray tube 21, the X-ray detector 22, the diaphragm 23, and the DAS 24 in one body around the object O, with the X-ray tube 21 and the X-ray detector 22 being opposed to each other.

The controller 26 includes a CPU (central processing unit) and a memory. The controller 26 controls the X-ray detector 22, the DAS 24, the high-voltage power supply 27, the diaphragm driving device 28, the rotation driving device 29, and the table-top driving device 31, etc. based on control signals input from the image processing system 12 such that scanning is executed.

The high-voltage power supply 27 supplies power needed for irradiation of X-rays, to the X-ray tube 21 through the control by the controller 26.

The diaphragm driving device 28 adjusts the irradiation range in the slice direction of X-rays at the diaphragm 23 through the control by the controller 26.

The rotation driving device 29 rotates the rotating portion 25 such that the rotating portion 25 rotates around a cavity portion with the positional relationship therebetween being maintained, through the control by the controller 26.

The table-top 30 can carry the object O.

The table-top driving device 31 moves the table-top 30 along the z-axis direction through the control by the controller 26. The central portion of the rotating portion 25 includes an opening, and the object O placed on the table-top 30 is inserted through the opening.

The image processing system 12 of the X-ray CT apparatus 1 includes a computer, and can perform two-way communication with a network N such as a LAN (local area network) of a hospital backbone network.

The image processing system 12 includes basic hardware such as, although not shown, a CPU, a memory, an HDD (hard disc drive), an input device, a display device, etc.

The image processing system 12 generates projection data by performing correction processing (preprocessing) such as logarithmic conversion processing, sensitivity correction, and the like on the raw data inputted from the DAS 24 of the scanner system 11. Moreover, the image processing system 12 performs eliminating processing of scattered rays on the preprocessed projection data. The image processing system 12, which is supposed to perform the elimination of scattered rays based on the value of the projection data within a range to be irradiated with X-rays, performs scattered ray correction by subtracting scattered rays estimated from the magnitude of the value of the target projection data to be subjected to scattered ray correction, or the adjacent projection data thereof, from target projection data. The image processing system 12 generates a reconstructed image based on the corrected projection data.

Figure 2:
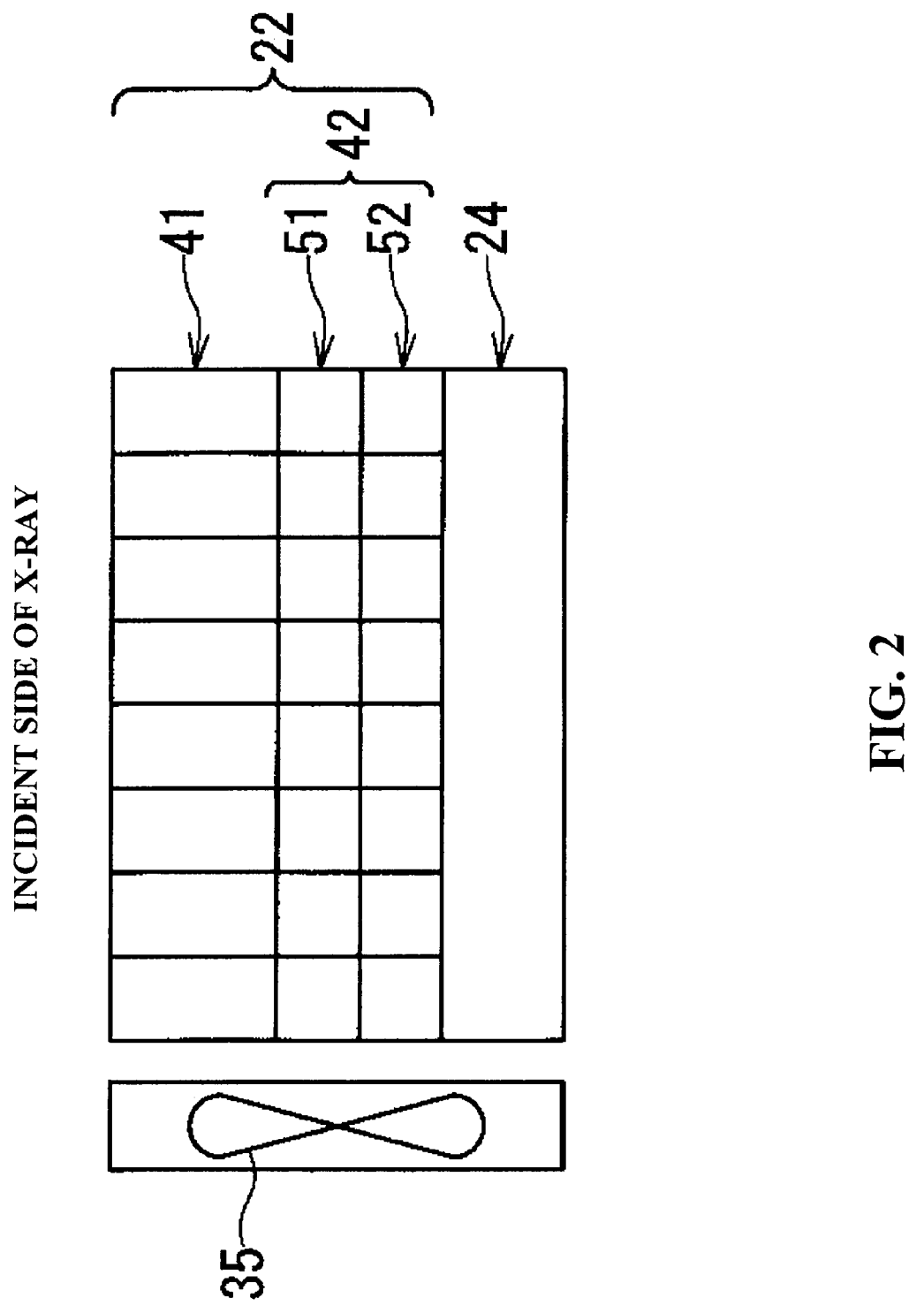
FIG. 2 is a side view showing an outline of a configuration of the periphery of an X-ray detector and a DAS in the X-ray CT apparatus of the embodiment.

FIG. 2 is a side view showing an outline of the configuration of the periphery of the X-ray detector 22 and the DAS 24 in the X-ray CT apparatus of the embodiment.

FIG. 2 shows an X-ray detector 22, a DAS 24, and a cooling fan 35 which is disposed in the periphery of the X-ray detector 22 and the DAS 24. The X-ray detector 22 includes a collimator (N collimators corresponding to N rows) 41 that collimates X-rays that have been transmitted through an object O, and a detection element (N detection elements corresponding to N rows) 42 that generates an electric signal based on the X-rays in a subsequent stage of the collimator 41. The detection element 42 includes a scintillator (N scintillators) 51, and a PDA (N PDAs) 52 to convert a fluorescence. It is noted that FIG. 2 shows, for example, a collimator 41 based on 8 collimators corresponding to 8 (N=8) rows, a scintillator unit 51 based on 8 scintillators corresponding to 8 (N=8) rows, and a PDA 52 based on 8 PDAs corresponding to 8 rows.

The DAS 24 is disposed integrally with the X-ray detector 22 in a subsequent stage of the PDA 52 such that the output surface of the X-ray detector 22 and the input surface of the DAS 24 are opposed to each other. It is noted that, although not shown, the DAS 24 can be disposed near the X-ray detector 22. The DAS 24 converts and amplifies an electric signal from the PDA 52 into a voltage signal, and further converts it into a digital signal.

The cooling fan 35 is attached to a substrate (not shown) of the DAS 24 to cool the DAS 24 (and the X-ray detector 22).

Figure 3:
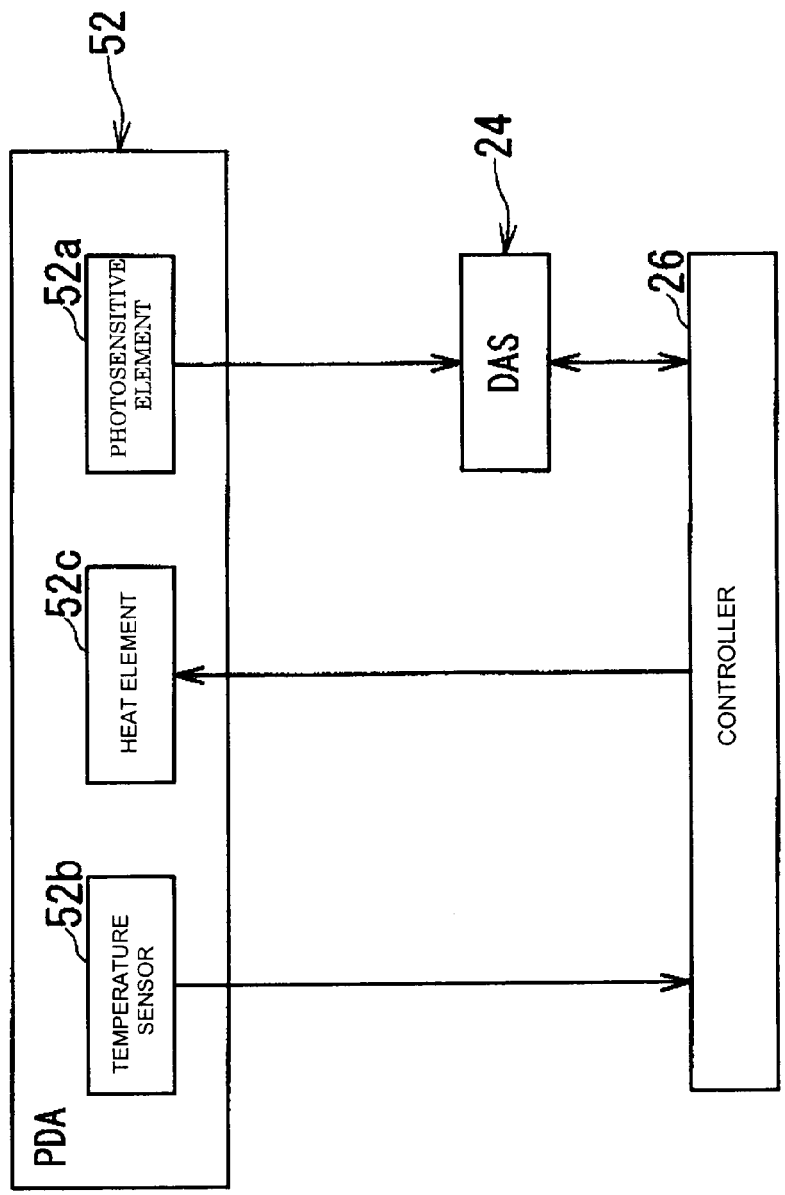
FIG. 3 is a schematic diagram showing a temperature sensor and a heat element of a PDA in the X-ray CT apparatus of the embodiment.

FIG. 3 is a schematic diagram showing a temperature sensor and a heat element of a PDA in the X-ray CT apparatus of the embodiment.

As shown in FIG. 3, the PDA 52 includes a photosensitive element (N photosensitive elements) 52a, a temperature sensor 52b, and a heat element (N heat elements) 52c. The temperature sensor 52b, in this embodiment produced by a semiconductor process, is embedded in the PDA 52. For example, the temperature sensor 52b is a CMOS (Complementary Metal Oxide Semiconductor) temperature sensor circuit, produced by a CMOS semiconductor process. A heat element 52c, in this embodiment produced by a semiconductor process, is embedded in the PDA 52.

The controller 26 receives temperature information signals from the temperature sensor 52b, and controls a temperature of the PDA 52, adjusting an electric current through the heat element 52c. In addition, the controller 26 receives the transmission data from the heat element 52c via the DAS 24.

The controller 26 controls the temperature of the PDA 52 through feedback control. The controller 26 adjusts the electric current through the heat element 52c when raising the temperature of the PDA 52.

On the other hand, the controller 26 adjusts at least one of the electric current through the heat element 52c or the volume of air of the cooling fan 35 when lowering the temperature of the PDA 52.

In this way, the temperature of the PDA 52 of the X-ray detector 22 is controlled within a range of, for example, about 40±1° C. which is higher than the room temperature, by the adjustments of the amount of the electric current flowing through the heat element 52c and the amount of air of the cooling fan 35. It is possible to maintain the image quality of the CT image that is generated by the image processing system 12 by controlling the temperature of the PDA 52.

Figure 4:
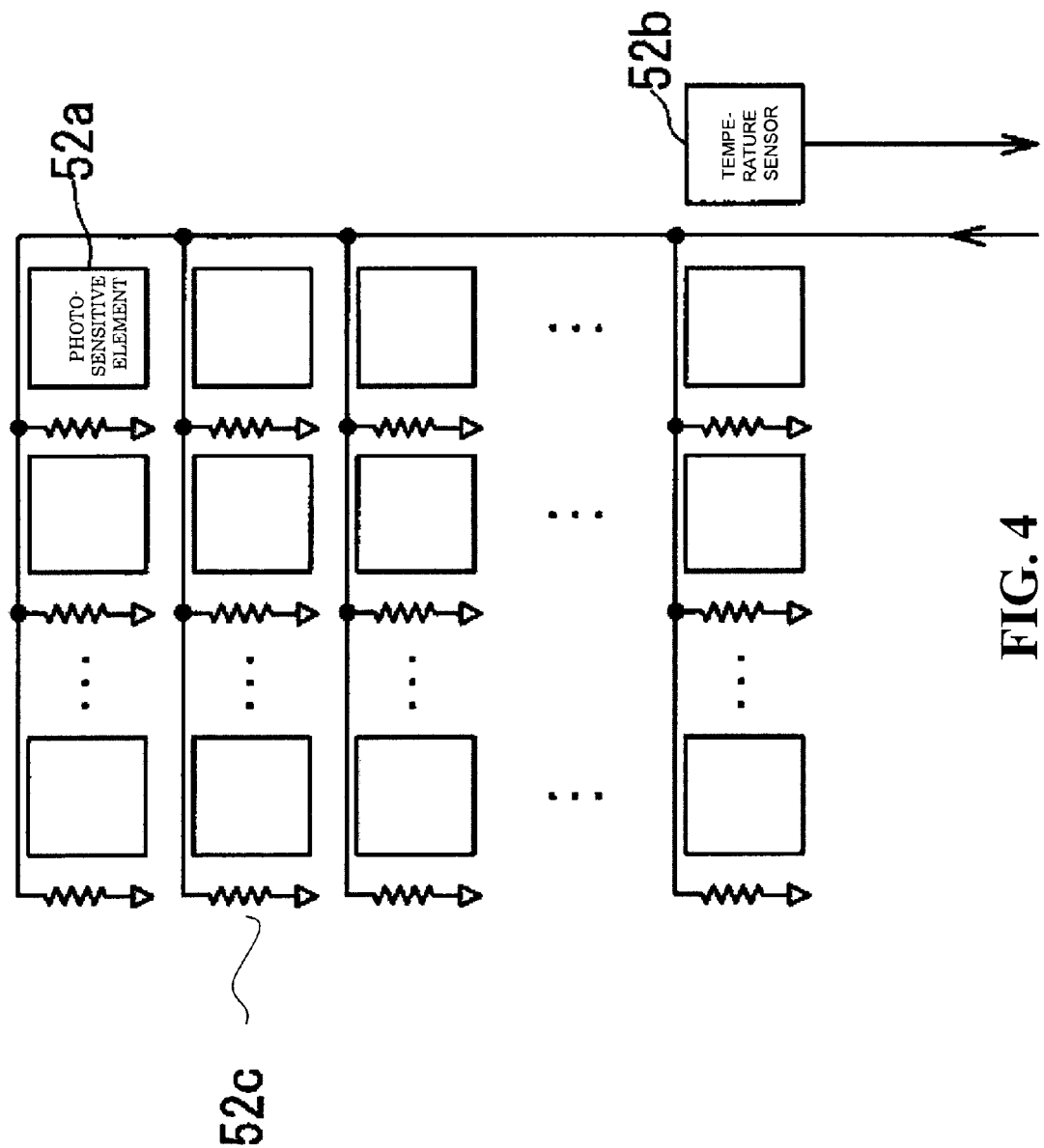
FIG. 4 is a top view showing a first configuration of the PDA in the X-ray CT apparatus of the embodiment.

FIG. 4 is a top view showing a first configuration of the PDA 52 in the X-ray CT apparatus of the embodiment.

As shown in FIG. 4, the PDA 52 includes the photosensitive elements 52a arranged in N×M, the temperature sensor 52b, and heat element 52c corresponding to the number of each photosensitive element 52a arranged in N×M.

In the case of the embodiment shown in FIG. 4, each heat element 52c of the PDA 52 is formed by a resistor element.

The number of the resistor elements can be not only the same number of the photosensitive elements 52a arranged in N×M, but can also be a different number.

So, in the configuration shown in FIG. 4, the controller 26 can adjust the amount of heat generation of the resistor elements, by adjusting the electric current through the resistor elements.

Figure 5:
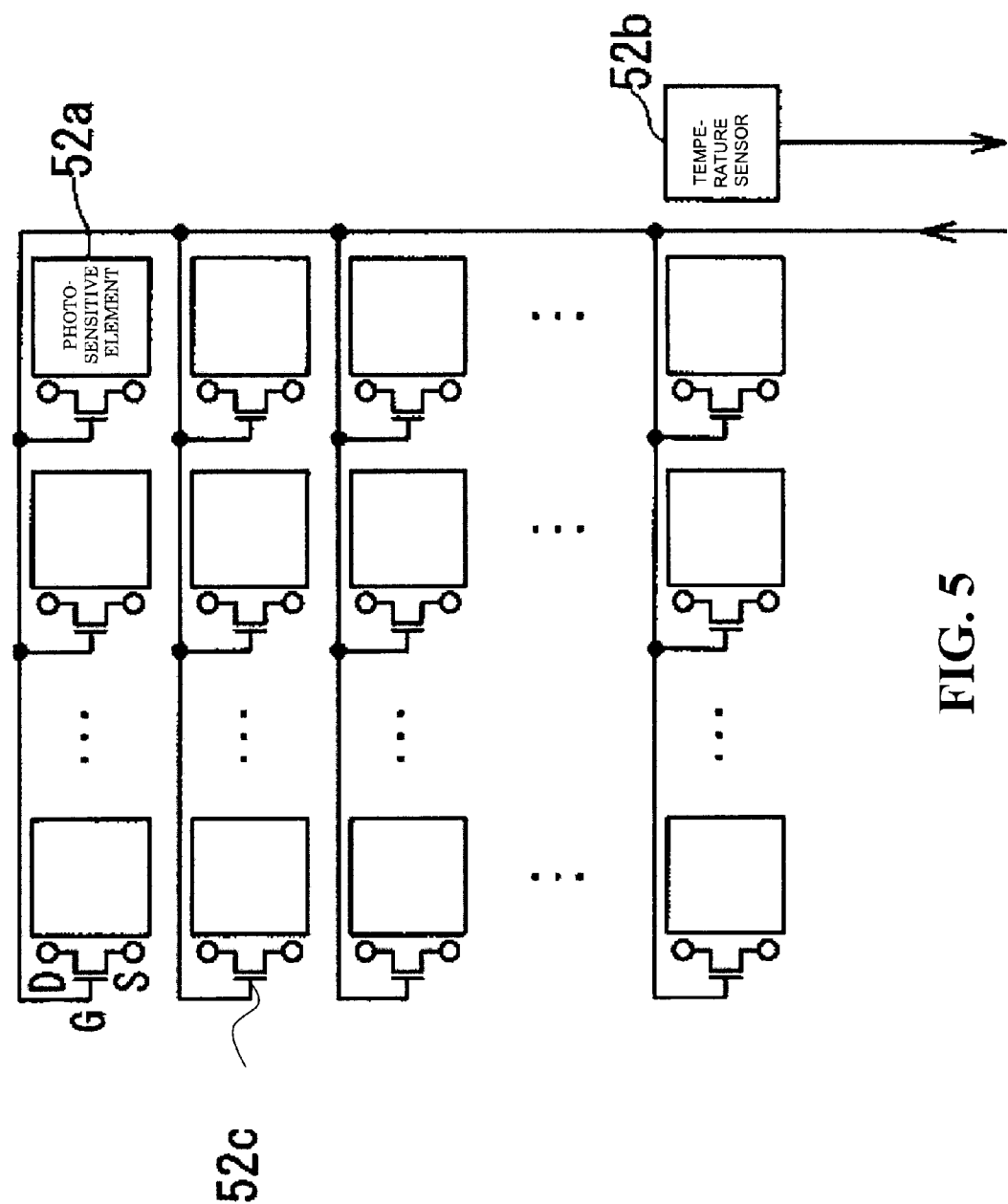
FIG. 5 is a top view showing a second configuration of the PDA in the X-ray CT apparatus of the embodiment.

FIG. 5 is a top view showing a second configuration of the PDA 52 in the X-ray CT apparatus of the embodiment.

As shown in FIG. 5, the PDA 52 arranged in N×M includes photosensitive elements 52a arranged in N×M, temperature sensor 52b, and heat elements 52c corresponding to the number of each photosensitive element 52a arranged in N x M. In the case of the embodiment shown in FIG. 5, each heat element 52c of the PDA 52 is a unipolar transistor, for example, a MOSFET transistor (Metal-Oxide-Semiconductor field-effect transistor).

The number of the MOSFET transistors can be not only the same number of the photosensitive elements 52a arranged in N×M, but can also be a different number.

The MOSFET transistor is a three terminal device including a positive supply voltage (Vdd) drain electrode (D), negative supply voltage (Vss) source electrode (S), and gate electrode (G). The MOSFET transistor may be a four terminal device further having a dual gate.

The heat element 52c is not limited to be a unipolar transistor. A bipolar transistor (not shown) is also available.

The bipolar transistor is a three terminal device including a base electrode (B), an emitter electrode (E), and a collector electrode (C).

When using the bipolar transistor, the controller 26 can control the electric current between the collector electrode (C) and the emitter electrode (E) by applying the current between the base electrode (B) and the emitter electrode (E).

In the configuration of the PDA 52 shown in FIG. 5, the controller 26 can adjust the current between source electrode (S) and drain electrode (D) by applying a voltage to the gate electrode (G) of each MOSFET transistor.

So, in the configuration shown in FIG. 5, the controller 26 can adjust the amount of heat generation of the MOSFET transistors, by adjusting the electric voltage applied the gate electrodes of the MOSFET transistors (N×M) as the heat element 52c.

Figure 6:
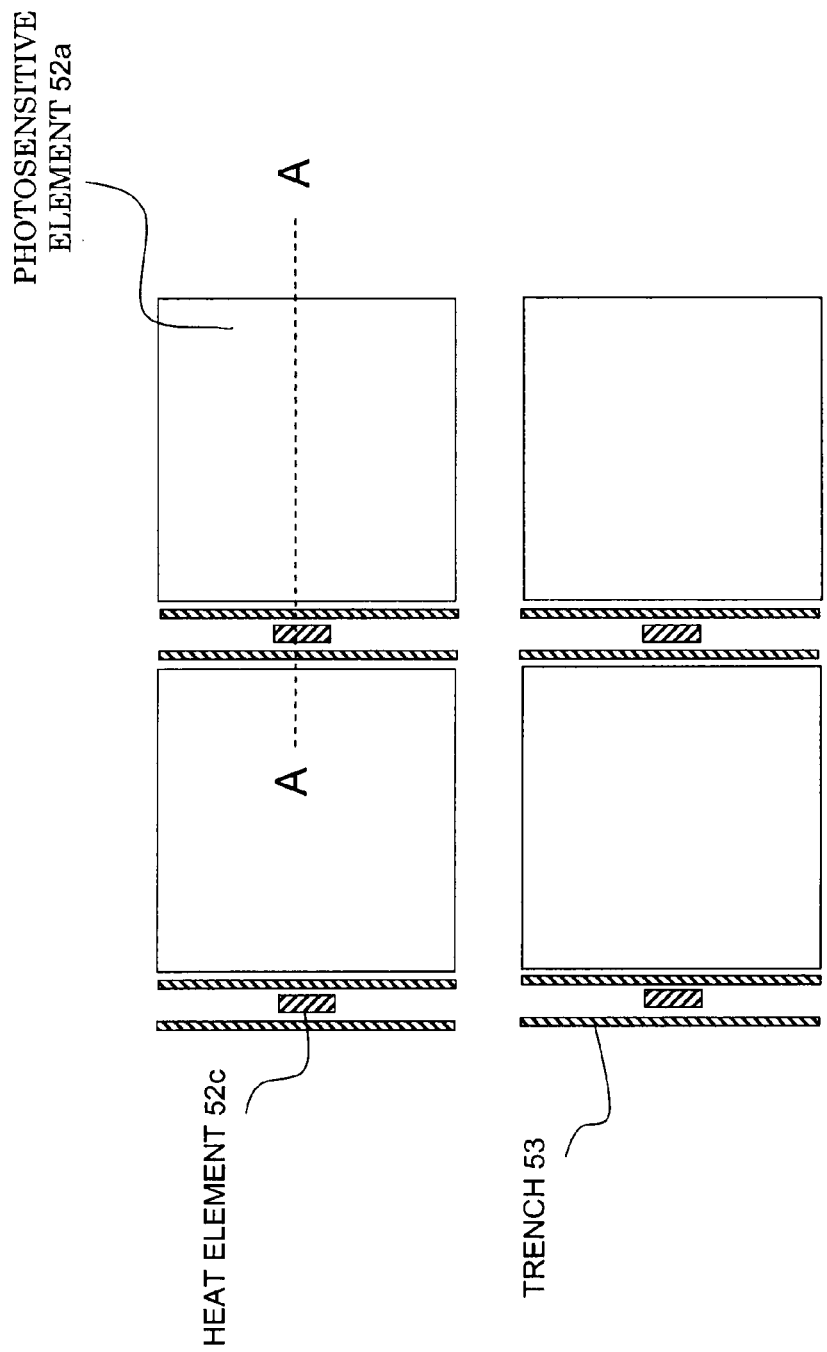
FIG. 6 is a plan view showing a configuration of a semiconductor trench in the X-ray CT apparatus of the embodiment.
Figure 7:
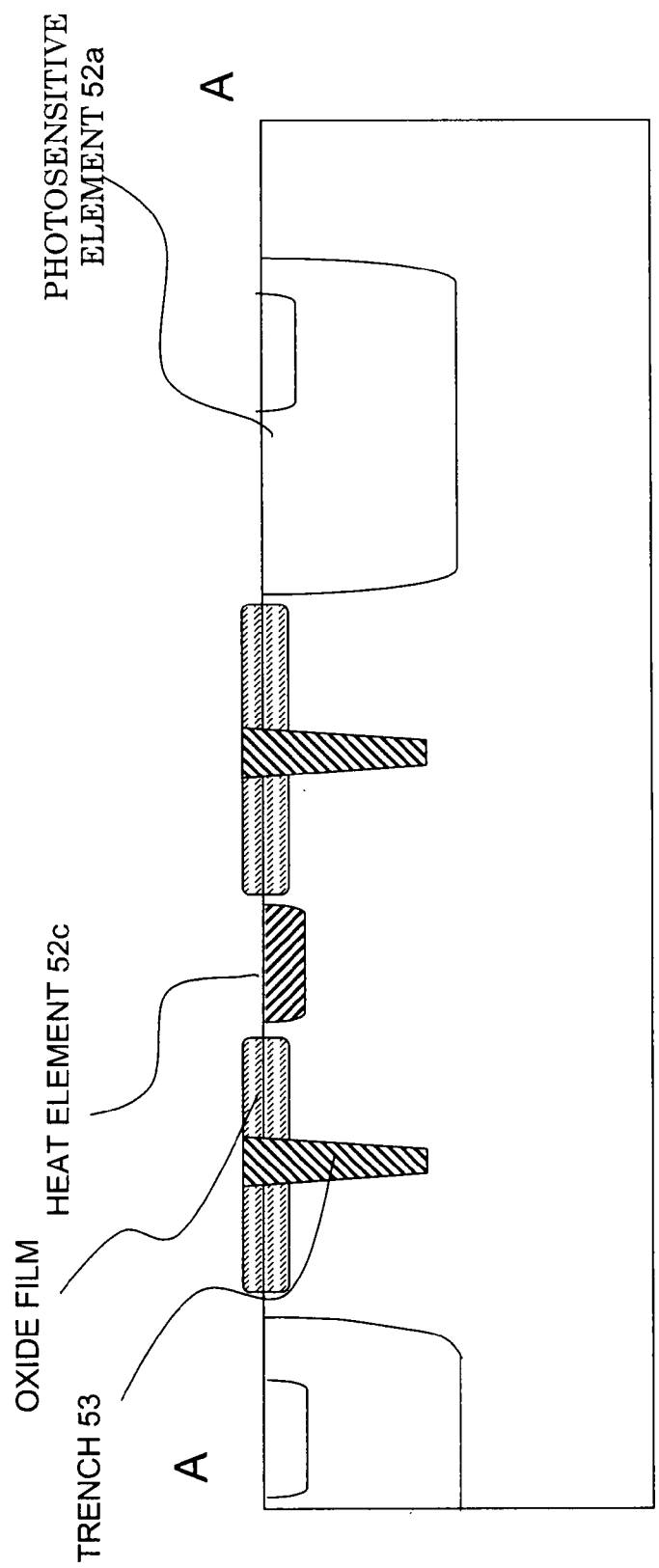
FIG. 7 is an enlarged sectional view, taken on section lines A-A of FIG. 6.

FIG. 6 is a plan view showing a configuration of a semiconductor trench in the X-ray CT apparatus of the embodiment, and FIG. 7 is an enlarged sectional view taken on section lines A-A of FIG. 6.

In this embodiment, a semiconductor trench 53 can be formed between the photosensitive element 52a and the heat element 52c. The semiconductor trench 53 is made of oxide silicon.

Figure 8:
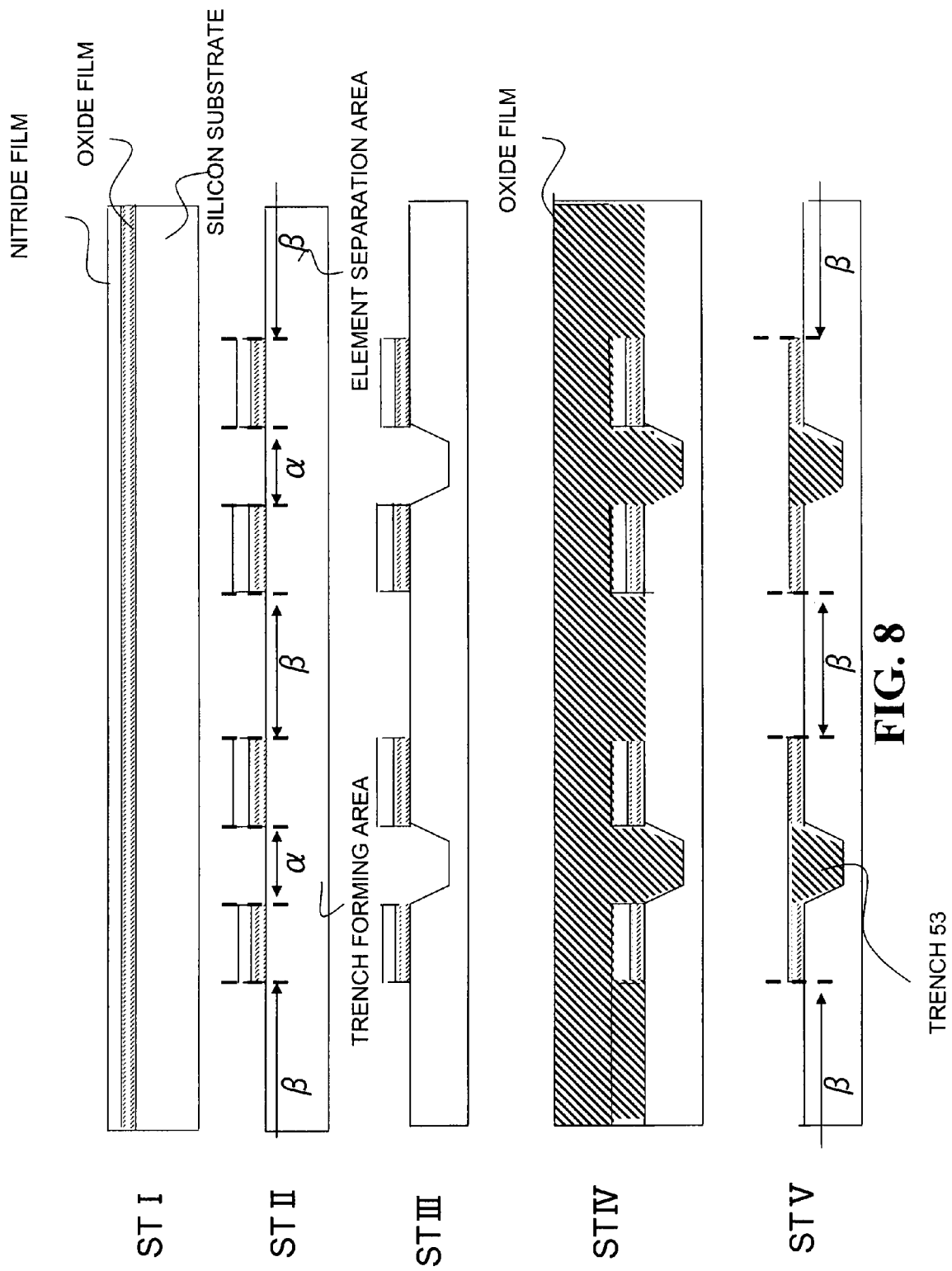
FIG. 8 is a schematic diagram showing a process of a semiconductor trench in the X-ray CT apparatus of the embodiment.

FIG. 8 is a schematic diagram showing a process of forming a semiconductor trench in the X-ray CT apparatus of the embodiment.

For instance, the trench 53 can be formed in the following process. First, a silicon substrate is heated in an oxide furnace at a temperature of about 1000 degrees C. to react with a oxide (O2). In this way, an oxide film (SiO2) is disposed on the silicon substrate. After this, a nitride film (SiN) is disposed on the oxide film (SiO2) by a CVD (Chemical Vapor Deposition) method (STEP STI).

Next, the oxide film (SiO2) and the nitride film (SiN) on a semiconductor trench forming area (α) an element separation area (β) are removed by a photolithography process (STEP STII).

After that, a shallow trench is formed on the semiconductor trench forming area (α) by dry etching process (STEP STIII).

And another oxide film (SiO2) is disposed on the silicon substrate by a CVD method (STEP IV).

Finally, the oxide film (SiO2) and the nitride film (SiN) are removed by a CMP (Chemical Mechanical Polishing) process, and the semiconductor trench 53 as an element separation area, and the element forming area (β) are formed (STEP STV).

The photosensitive element 52a and the heat element 52c can be formed on the element forming area (β).

Using the semiconductor trench 53 of this embodiment achieves the element separation area between the photosensitive element 52a and the heat element 52c. This separation permits the photosensitive element 52 to prevent a thermal noise (Johnson Noise) from interfering with image signals.

Figure 9:
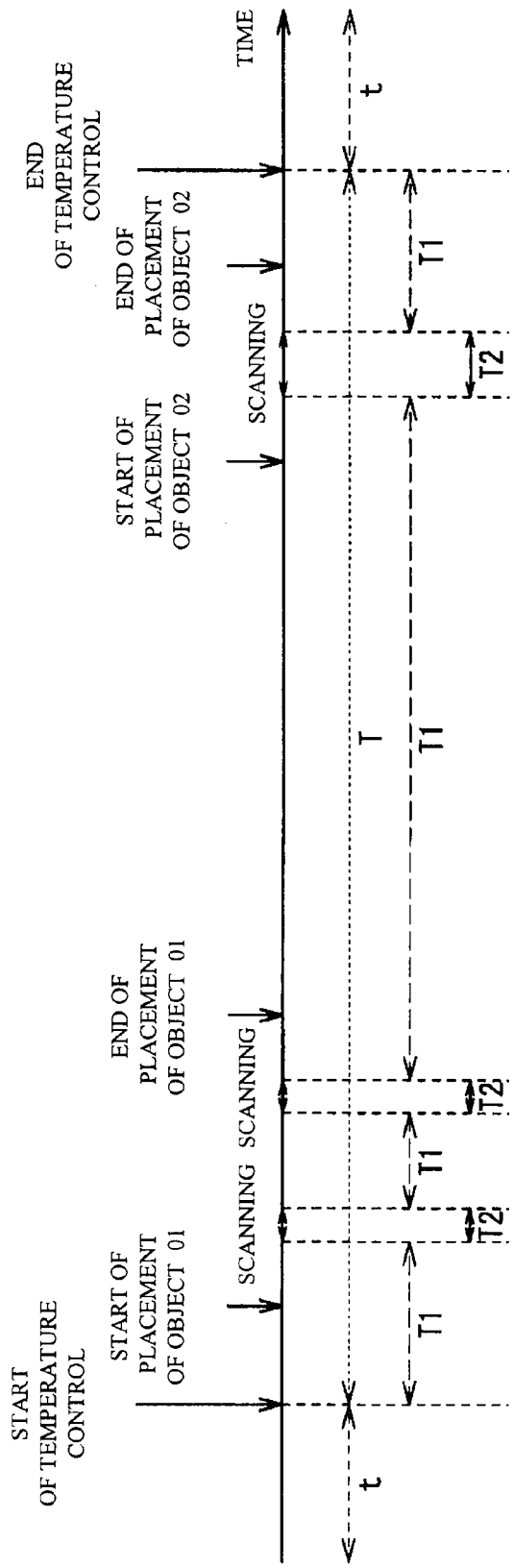
FIG. 9 is a diagram showing an example of a time chart to illustrate an operation of the X-ray CT apparatus of the embodiment.

FIG. 9 is a diagram showing an example of the time chart to illustrate the operation of an X-ray CT apparatus of the embodiment.

As shown in FIG. 9, the X-ray CT apparatus 1 performs two scanning operations (for example, conventional scanning) after starting the placement of an object O1 on a table-top 30, thereafter ending the placement of the object O1.

Successively, the X-ray CT apparatus 1 performs one scanning operation (for example, helical scanning) after starting the placement of an object O2 on the table-top 30, thereafter ending the placement of the object O2. The X-ray CT apparatus 1 ends the operation after the scanning of the object O2.

In a temperature non-controlled period t shown in FIG. 9, since the controller 26 does not control the temperature of the PDA 52 and no scanning is executed as well, the temperature of the room in which the X-ray CT apparatus is installed becomes a major disturbance, and the temperature of the PDA 52 converges to the room temperature.

The period other than the temperature non-controlled period t is a temperature controlled period T. In a non-scanning period (scanning standby period) T1 which is in the temperature controlled period T, the temperature of the room in which the X-ray CT apparatus is installed becomes a major disturbance so that the temperature of the PDA 52 converges to the room temperature.

Accordingly, in the non-scanning period T1, the controller 26 performs a feedback control of the PDA 52, which is repeatedly detected by the temperature sensor 32, as the controlled object, with an appropriate temperature of the PDA 52 as the target value and with the amount of the current flowing through the heat element 52c as the manipulated variable. For example, the controller 26 performs a PID control of the temperature of the PDA 52.

On the other hand, in a scanning period T2 which is in a temperature controlled period T, the exhaust heat of the DAS 24 becomes a major disturbance, and can effect the temperature of the PDA 52. In the scanning period T2, the controller 26 performs a feedback control of the temperature of PDA 52, which is repeatedly detected by the temperature sensor 52b, as a controlled object, with an appropriate temperature of the detection element unit 42 as the target value and with at least one of the amount of the current flowing through the heat element 52c and the amount of air of the cooling fan 35 as the manipulated variable. For example, the controller 26 performs a PID control of the temperature of the PDA 52.

Figure 10:
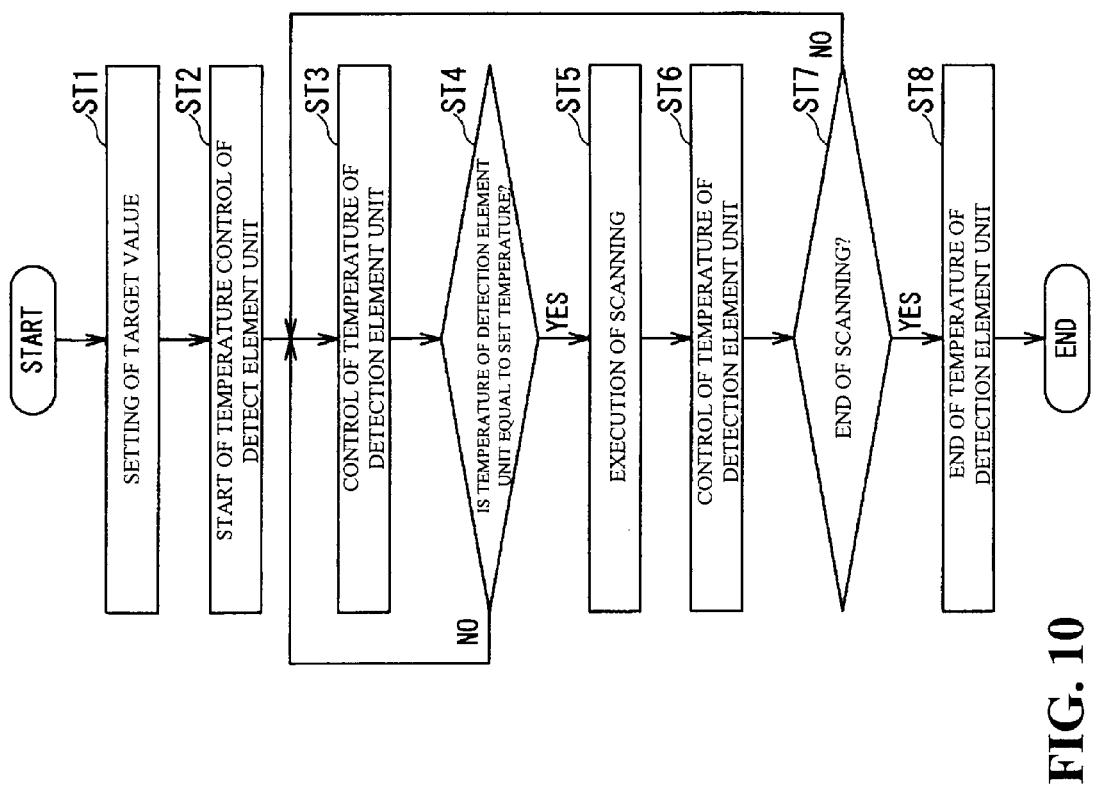
FIG. 10 is a flowchart showing the operation of the X-ray CT apparatus of the embodiment.
Figure 11:
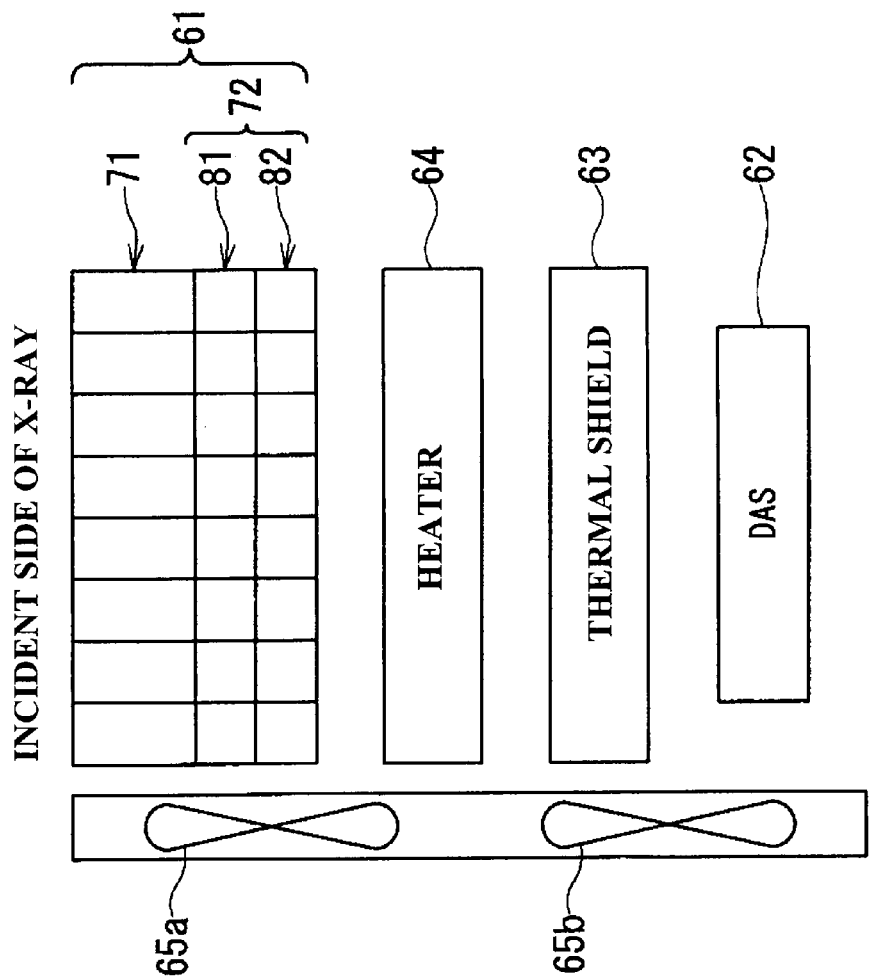
FIG. 11 is a side view showing an outline of a configuration of a periphery of an X-ray detector and a DAS in a background X-ray CT apparatus.

Next, the operation of the X-ray CT apparatus 1 of the embodiment will be described by using a flowchart shown in FIG. 10.

First, the controller 26 of the -ray CT apparatus 1 sets an appropriate temperature of the PDA 52 of the X-ray detector 22, as a target value (step ST1). When an operator inputs, for example, a range of 40±1° C. through an input device (not shown) of the image processing system 12, the controller 26 sets the range of 40±1° C. as the target value.

Next, upon input by the operator through the input device (not shown) of the image processing system 12, the controller 26 starts the control of the temperature of the PDA 52 (step ST2). When the temperature control of the PDA 52 is started at step ST2, the X-ray CT apparatus 1 comes into a standby state waiting for scanning.

That is, using FIG. 9, the X-ray CT apparatus 1 makes a transition from a temperature non-control period t to a non-scanning period T1 which is a temperature controlled period T.

In the non-scanning period T1, the controller 26 adjusts the amount of the current flowing through the heat element 52c with an appropriate temperature set at step ST1 as the target value. That is, the controller 26 adjusts the amount of heat generation of the heat element 52c, and controls the temperature of the PDA 52 (step ST3). For example, in step ST3, a PID control of the temperature of the PDA 52 is performed with the amount of the current flowing through the heat element 52c as the manipulated variable.

Next, upon receiving an instruction to start scanning, the controller 26 determines whether or not the temperature of the PDA 52 detected by the temperature sensor 52b is equal to the target value set at step ST1 (step ST4).

When the determination at step ST4 is YES, that is, it is determined that the temperature of the PDA 52 detected by the temperature sensor 52b is equal to the target value set at step ST1, the controller 26 executes scanning (step ST5). That is, using FIG. 9, the X-ray CT apparatus 1 makes a transition from a non-scanning period T1 to a scanning period T2.

In the scanning period T2, the controller 26 adjusts at least one of the amount of the current flowing through the heat element 52c and the amount of air of the cooling fan 35 based on the temperature of the PDA 52, which are repeatedly detected with the temperature sensor 52b, with the appropriate temperature set at step ST1 as the target value. That is, the controller 26 controls the temperature of the PDA 52 (step ST6). For example, in step ST6, a PID control of the temperature of the PDA 52 is performed with at least one of the amount of the current flowing through the heat element 52c and the amount of air of the cooling fan 35 as the manipulated variable.

On the other hand, when the determination at step ST4 is NO, that is, it is determined that the temperature of the PDA 52 detected with the temperature sensor 52b is not equal to the target value set at step ST1, the controller 26 controls the temperature of the PDA 52 until the temperature of the PDA 52 reaches the target value set at step ST1 (step ST3).

After the step ST6, the controller 26 determines whether or not to end the control of the temperature of the PDA 52 (step ST7). When the determination at step ST7 is YES, that is, it is determined to end the control of the temperature of the PDA 52, the controller 26 ends the operation (step ST8).

That is, using FIG. 9, the X-ray CT apparatus 1 makes a transition from a scanning period T2 to a temperature non-controlled period t. For example, when all the scanning to be performed in a certain day is finished, and an operator inputs an instruction to end the process through an input device (not shown) of the image processing system 12, the controller 26 determines to end the control of the temperature of the PDA 52.

On the other hand, when the determination at step ST7 is NO, that is, it is determined not to end the control of the temperature of the PDA 52, that is, to continue the scanning, the controller 26 again controls the temperature of the PDA 52 (step ST3). That is, using FIG. 9, the X-ray CT apparatus 1 makes a transition from a scanning period T2 to a non-scanning period T1.

According to the X-ray CT apparatus 1 of the embodiment, it is possible to facilitate the temperature control of the PDA 52 with a simple structure, thereby improving the image quality of a CT image, and allowing the temperature control to be applied particularly to a case in which the X-ray detector 22 and the DAS 24 are configured to be adjacent structures, or a unitary structure.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
   an X-ray source configured to generate an X-ray;
   a scintillator configured to convert the X-ray into a fluorescent;
   a photodiode array including a plurality of photosensitive elements, formed on a substrate, configured to convert the fluorescent into an electric charge, a plurality of heat elements formed on the substrate, and a heat sensor formed on the substrate, at least one of the heat elements positioned between adjacent ones of the photosensitive elements; and
   a controller configured to control an amount of heat generation of the plurality of heat elements by adjusting an electric current of the heat elements or an electric voltage of the heat elements on the basis of temperature information from the heat sensor.

2. The X-ray CT apparatus according to claim 1, further comprising a semiconductor trench formed on the substrate.

3. The X-ray CT apparatus according to claim 2, wherein the semiconductor trench is formed between the heat sensor and the heat elements.

4. The X-ray CT apparatus according to claim 3, further comprising a cooling fan.

5. The X-ray CT apparatus according to claim 4, wherein the controller further controls the temperature of the plurality of photosensitive elements by adjusting a volume of air of the cooling fan.

6. The X-ray CT apparatus according to claim 5, wherein the controller adjusts the temperature of the plurality of photosensitive elements so as to be a target value in a non-scanning period.

7. The X-ray CT apparatus according to claim 3, wherein the heat sensor and the heat elements are semiconductor elements.

8. The X-ray CT apparatus according to claim 7, wherein the heat sensor and the heat elements are semiconductor elements on a semiconductor element forming area.

9. The X-ray CT apparatus according to claim 3, wherein the heat elements are resistor elements.

10. The X-ray CT apparatus according to claim 3, wherein the heat elements are Unipolar elements.

11. The X-ray CT apparatus according to claim 3, wherein the heat elements are MOSFET transistors.

12. The X-ray CT apparatus according to claim 3, wherein the heat elements are bipolar transistors.

13. The X-ray CT apparatus according to claim 1,
    wherein a number of the heat elements corresponds to a number of the photosensitive elements.

* * * * *